United States Patent
Jiang (10) Patent No.: US 7,310,147 B2
(45) Date of Patent: Dec. 18, 2007

(54) ROBOTIC APPARATUS FOR PICKING OF CELLS AND OTHER APPLICATIONS WITH INTEGRATED SPECTROSCOPIC CAPABILITY

(75) Inventor: Yonggang Jiang, New Milton (GB)

(73) Assignee: Genetix Limited, New Milton (GB)

( * ) Notice: Subject to any disclaimer, the term of this patent is extended or adjusted under 35 U.S.C. 154(b) by 358 days.

(21) Appl. No.: 11/050,818

(22) Filed: Jan. 27, 2005

(65) Prior Publication Data
US 2006/0164644 A1 Jul. 27, 2006

(51) Int. Cl.
*G01J 3/44* (2006.01)
*G01N 21/64* (2006.01)
*G01N 21/65* (2006.01)

(52) U.S. Cl. .............. 356/417; 356/418; 356/301; 250/458.1; 422/82.08; 435/288.7; 436/172

(58) Field of Classification Search ............. 356/417, 356/418; 435/288.7
See application file for complete search history.

(56) References Cited

U.S. PATENT DOCUMENTS

| | | | |
|---|---|---|---|
| 5,397,709 | A | 3/1995 | Berndt |
| 5,690,417 | A | 11/1997 | Polidor et al. |
| 6,165,734 | A | 12/2000 | Garini et al. |
| 6,400,487 | B1 | 6/2002 | Harris et al. |
| 6,690,470 | B1 | 2/2004 | Baer et al. |
| 6,743,576 | B1 | 6/2004 | Sabry et al. |
| 6,746,864 | B1 * | 6/2004 | McNeil et al. ........... 435/288.7 |
| 6,823,079 | B1 | 11/2004 | Winterot et al. |
| 6,905,838 | B1 | 6/2005 | Bittner |
| 2003/0059820 | A1 | 3/2003 | Vo-Dinh |
| 2003/0082516 | A1 | 5/2003 | Straus |
| 2003/0179916 | A1 | 9/2003 | Magnuson et al. |
| 2004/0178370 | A1 | 9/2004 | Oldham et al. |
| 2005/0105172 | A1 | 5/2005 | Hasegawa et al. |

(Continued)

FOREIGN PATENT DOCUMENTS

EP 1 180 679 A1 2/2002

(Continued)

OTHER PUBLICATIONS

De Blasio et al., "Combining Optical and Electrical Impedance Techniques for Quantitative Measurement of Confluence in MDCK-I cell cultures," *BioTechniques*, vol. 36, No. 4, pp. 650-661 (Apr. 2004).

*Primary Examiner*—F. L. Evans
(74) *Attorney, Agent, or Firm*—Foley & Lardner LLP (57) ABSTRACT

A robotic apparatus of the kind having a sample manipulation head with associated positioning system mounted above the main bed of the apparatus, as used for picking of cells, in particular animal cells, or for other biological or chemical applications. An imaging station is arranged on the main bed where a sample container containing a sample can be placed in an object position. According to the invention, both excitation and collection optical sub-systems are mounted under the main bed of the apparatus for performing spectroscopic analysis on a sample at the imaging station. The integration is based on a reflection mode optical solution, which allows all the optical components to be mounted under the main bed of the apparatus. Consequently, ancillary software driven or manual processes can be carried on with whether or not spectroscopic measurements are being made.

69 Claims, 9 Drawing Sheets

U.S. PATENT DOCUMENTS

2006/0258018 A1    11/2006    Curl et al.

FOREIGN PATENT DOCUMENTS

| | | |
|---|---|---|
| EP | 1 293 783 A2 | 3/2003 |
| EP | 1 351 048 A1 | 10/2003 |
| EP | 1 391 719 A2 | 2/2004 |
| JP | 2004-354347 | 12/2004 |
| WO | WO 92/12233 | 7/1992 |
| WO | WO 01/69206 A1 | 9/2001 |
| WO | WO 01/77648 A1 * | 10/2001 |
| WO | WO 2004/061425 A1 | 7/2004 |

* cited by examiner

ROBOTIC APPARATUS FOR PICKING OF CELLS AND OTHER APPLICATIONS WITH INTEGRATED SPECTROSCOPIC CAPABILITY

BACKGROUND OF THE INVENTION

The invention relates to a robotic apparatus for picking of cells, in particular animal cells, or for other biological or chemical applications, such as gel coring or well plate liquid handling, with integrated spectroscopic capability for fluorescence studies, colorimetry and the like.

It is common practice to use fluorescent markers to identify biological or chemical material. Traditionally, these fluorescent markers are investigated using a stand-alone imaging device, referred to as an imager. Two types of imager are now briefly described.

Figure 6:
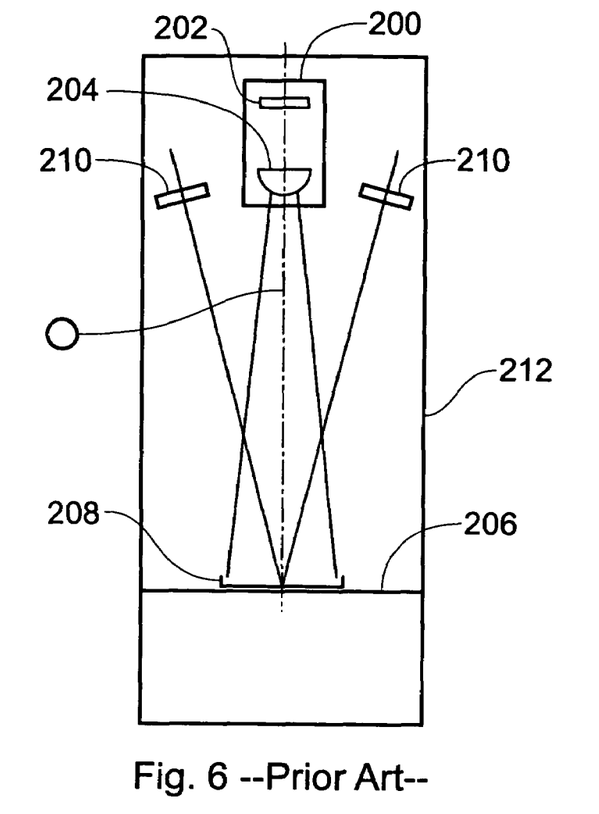
FIG. 6 shows a prior art imager.

FIG. 6 is a schematic side view of an imager in which a charged coupled device (CCD) detector unit 200 comprising a CCD chip 202 and objective 204 is arranged above a shelf 206 on which a sample dish 208 can be placed centrally about the optical axis "O" of the CCD detector unit 200. Alongside the CCD detector unit 200, banks of blue light emitting diodes (LEDs) 210 are arranged facing the center of the shelf where sample dishes are to be placed. The blue LED banks 210 are used to excite fluorescence in the sample which is then measured by the CCD chip. The imager is built into a light-tight housing 212 accessed by a hinged door (not shown). An imager of this kind is the Fuji LAS-1000.

Figure 7:
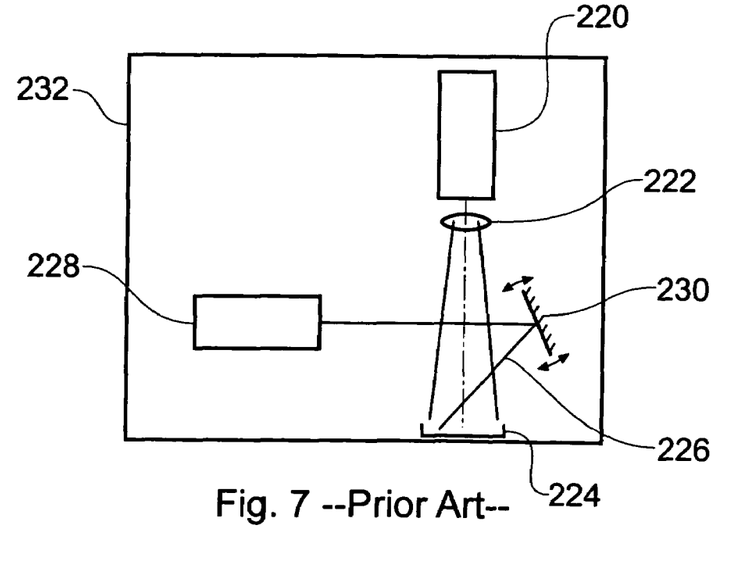
FIG. 7 shows a further prior art imager.

FIG. 7 is a schematic side view of a scanning imager in which a photomultiplier tube (PMT) 220 and objective 222 are used to measure fluorescence from a sample contained in a sample dish 224 which is excited by raster scanning a 488 nm laser beam 226 generated by an argon ion laser 228 over the sample dish. Raster scanning is achieved by a movable mirror arrangement 230. The scanner is arranged in a light tight housing 232.

In some circumstances it would be desirable to integrate an imaging capability into a robot used for handling well plates or other biological sample containers such as Q-trays, omni-trays, Petri dishes and so forth. This would avoid having to move samples between the robot and the imager. To satisfy this need, a gel picking robot with an integrated imager is known as now described.

Figure 8:
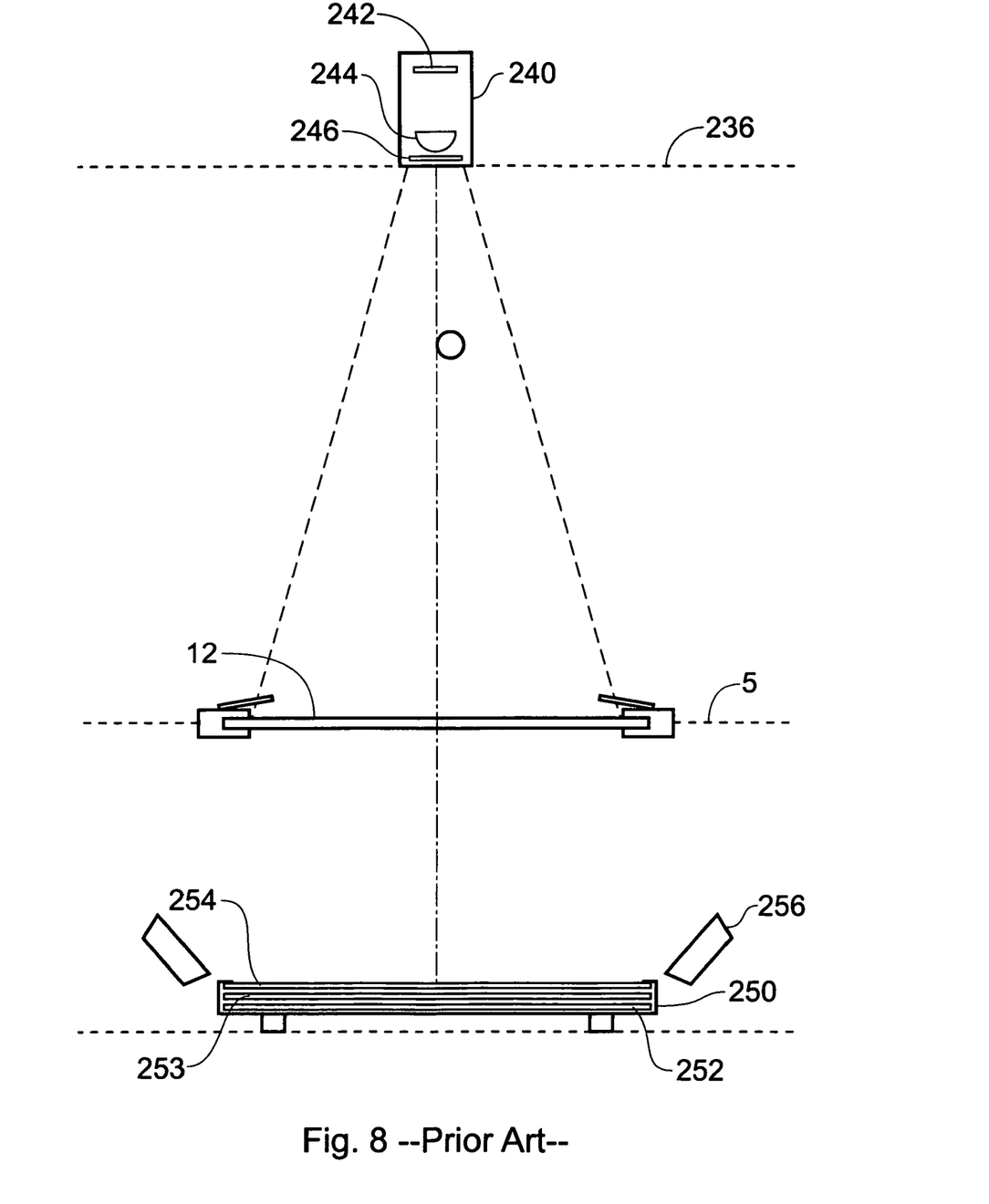
FIG. 8 shows a prior art gel coring robot with integrated imager.

FIG. 8 shows a robot for imaging and excision of fluorescent gels according to EP-A-1391719 [1]. A detector unit 240 is mounted in the roof 236 of the robot to image down onto a gel dish placed on a light table. The detector unit 240 contains a CCD chip 242 with associated collection optics 244 and bandpass filter 246. In the middle of the figure, the light table plate 12 is illustrated which lies in the plane of the robot's main bed 5. The light source unit 250 is mounted below the main bed of the apparatus and is based on banks of LEDs 252 whose light is filtered with a filter 253 and homogenised with a diffuser 254. Fluorescence is excited by illuminating the light table from below with the LEDs 252. It is therefore possible to perform fluorescence analysis and gel coring (excision) using the same machine.

Although this design based on transmission-mode optics has been successful, and importantly allows the conventional layout of a microarraying or picking robot to be maintained, the mounting of the detection optics (i.e. the CCD camera) in the roof of the robot with the collection light path extending between the bed of the robot and the roof of the robot is sometimes inconvenient. In particular the robot head and its positioning motors and associated gantries need to be moved out of the way when making fluorescence measurements to avoid blocking the collection light path.

SUMMARY OF THE INVENTION

The invention provides a robotic apparatus comprising: a main bed fitted with an imaging station where a sample container containing a sample can be placed in an object position; a head with associated positioning system mounted above the main bed of the apparatus; and excitation and collection optical sub-systems mounted under the main bed of the apparatus and arranged to excite, and collect light from, the object position from below.

The invention can thus provide a robot with integrated excitation and collection optical sub-systems for performing fluorescence analysis mounted under the main bed of the apparatus. The integration is based on a reflection mode optical solution, which allows all the optical components to be mounted under the main bed of the apparatus. Consequently, ancillary software driven or manual processes can be carried on with whether or not fluorescence measurements are being made. In particular, the robot head is free to move around the main bed of the apparatus without passing through the light excitation or collection paths from the source and detector respectively.

The excitation optical sub-system is preferably controllable to provide excitation at any one of a plurality of different wavelengths for selectively exciting a plurality of different dyes of interest. This may be done by providing a plurality of different types of optical source of different emission wavelengths, such as with different sources mounted at different "filter" positions on a filter wheel. Alternatively a tunable source may be used.

The excitation optical sub-system preferably comprises a plurality of different bandpass filters for selecting light at different wavelengths for selectively exciting a plurality of different dyes of interest. This may be used in combination with a plurality of optical sources of different wavelength, with each filter being paired with a particular source. Alternatively, the filters may be used to filter a single broadband source to select a wavelength range targeted at a particular dye.

The excitation optical sub-system may comprise a white light source which may be used either as a fluorescence excitation source or for contrast imaging, or both.

The excitation optical sub-system may comprise one or more optical sources arranged to illuminate the object position at an oblique angle, preferably in the range 10-50 or 20-40 degrees to the horizontal. With oblique illumination, the collection optical sub-system can advantageously be arranged to collect light from the object position such that the light is collected in a dark field configuration where light from the obliquely illuminating optical source, if not scattered, does not contribute to the collected signal.

The collection optical sub-system preferably comprises a plurality of different filters for assisting collection of light at different emission wavelengths associated with fluorescence from a plurality of different dyes of interest. Typically this will be by acting to block light at the excitation wavelength used to excite fluorescence in the dye being used, and to transmit light at the emission wavelength of that dye. These collection-side filters may be mounted on a filter wheel to allow automated selection via a central control system.

The apparatus preferably also includes an optics positioning system for aligning the excitation and collection optical sub-systems relative to the object position so that any desired location of the sample container can be moved into the object position. For example, if the sample container is a well plate, the control system can then be operated to position each well in turn at the object position in a rastering type process by column and row. Another example would be if the sample container is a large-area container such as a Petri dish containing colonies positioned at known locations, the control system can be operated to position each of a sequence of previously identified colonies in turn at the object position.

The excitation optical sub-system in some embodiments comprises a plurality of directional light emitting units arranged to emit beams having optical axes lying on the surface of a common cone, the point of which is coincident with the object position. This idea may be extended such that the optical source comprises a plurality of directional light emitting units arranged to emit beams having optical axes lying on the surface of at least two cones whose points are coincident with each other and the object position.

The apparatus can conveniently be provided with a sample container feeder/stacker, such as for well plates, operable to supply each of a plurality of sample containers from a feed and return them to a stack.

The head will typically comprise a plurality of elements for performing a sample manipulation task, such as solid or split pins for picking, hollow pin gel corers, micropipette types for liquid handling and so forth.

The invention in another aspect relates to use of a robot equipped with a head for manipulating biological samples, the use comprising: providing a sample container containing at least one cell; arranging the sample container at an imaging station; making a spectroscopic measurement by illuminating the at least one cell from below and collecting light from the at least one cell also from below; and manipulating the at least one cell with the head based on the spectroscopic measurement.

There may be a single cell in the sample container, a number of individual cells, or cells formed in one or more colonies. The at least one cell may be an animal cell. The robot may be used for fluorescence studies, including bioluminescence, chemiluminescence and so forth, as well as for colorometric studies, for example of red colonies. The cell or cells may express a biological molecule of interest. The biological molecule of interest can be selected from the group consisting of: a peptide, a polypeptide, a nucleic acid, a lipid, a metabolyte, or a glycosylated or unglycosylated protein. The biological molecule of interest may be a biopharmaceutical protein.

The cell or cells may themselves be marked with the dye, or contained in a medium which is marked with the dye whose optical activity is modified by secretion from the at least one cell. Example uses include assaying of individual cells or clones of cells for genetic changes by means of phenotypic markers that can be detected by changes within the cell or as a consequence of secretion from the cell or a combination of both. Examples include the identification of protease activities associated or missing from a cell by measuring the change in color or emission wavelength of an indicator in the medium. For example a quenched substrate within the medium may not exhibit fluorescence until it is cleaved by an enzyme or other activity. Measurements of changes in fluorescence with the robot are made to detect the activity. It will be understood that there are numerous assays applicable to these kinds of measurements, for example those exemplified in the Molecular Probes catalog.

The apparatus of the invention provides a versatile platform for this and a variety of other uses based around fluorescence measurements which may be spatially resolved within each measurement (fluorescence imaging) or may be limited to a single spectroscopic analysis for the data collected at each sample position, for example a single analysis for each well of a well plate.

The apparatus can be used to pick valuable or interesting cells or colonies of cells from a cell population. The cells may be 1 to 50 in number in the case of individual cells, or much greater in number in the case of colonies. Using the apparatus such cells can be picked according to spectroscopic criteria. A cell may contain a compound that is present in greater or lesser amounts than the population as a whole. An example may be a cell or colony that has a high level of GFP (detected by fluorescence), a high level of metabolite (detected by Raman) or a pigment (detected by white light). These would all be endogenous. However, it is also possible to detect cells or clones that have altered spectral properties by adding exogenous reagents or compounds and measuring, using spectroscopic analysis, changes in spectral properties of a cell or colony or a component thereof. Examples would include adding a quenched dye to cells then stimulating the cells physiologically and using spectral changes (such as fluorescence) to measure calcium levels (Fura-2) or pH. The apparatus could then pick those colonies (based on the amount of emission or wavelength of the emission) that are high or low expressers.

Furthermore these spectral changes may be observed not only in the cells but also outside the cells as a consequence of components secreted into the medium from the cell. The components can be detected either directly, indirectly by the addition of a component such as a fluorescent antibody, or by an effect the component has upon the medium. There is also the case where the component straddles the membrane of the cell so is both inside and outside the cell.

BRIEF DESCRIPTION OF THE DRAWINGS

For a better understanding of the invention and to show how the same may be carried out reference is now made by way of example to the accompanying drawings in which.

DETAILED DESCRIPTION

Figure 1:
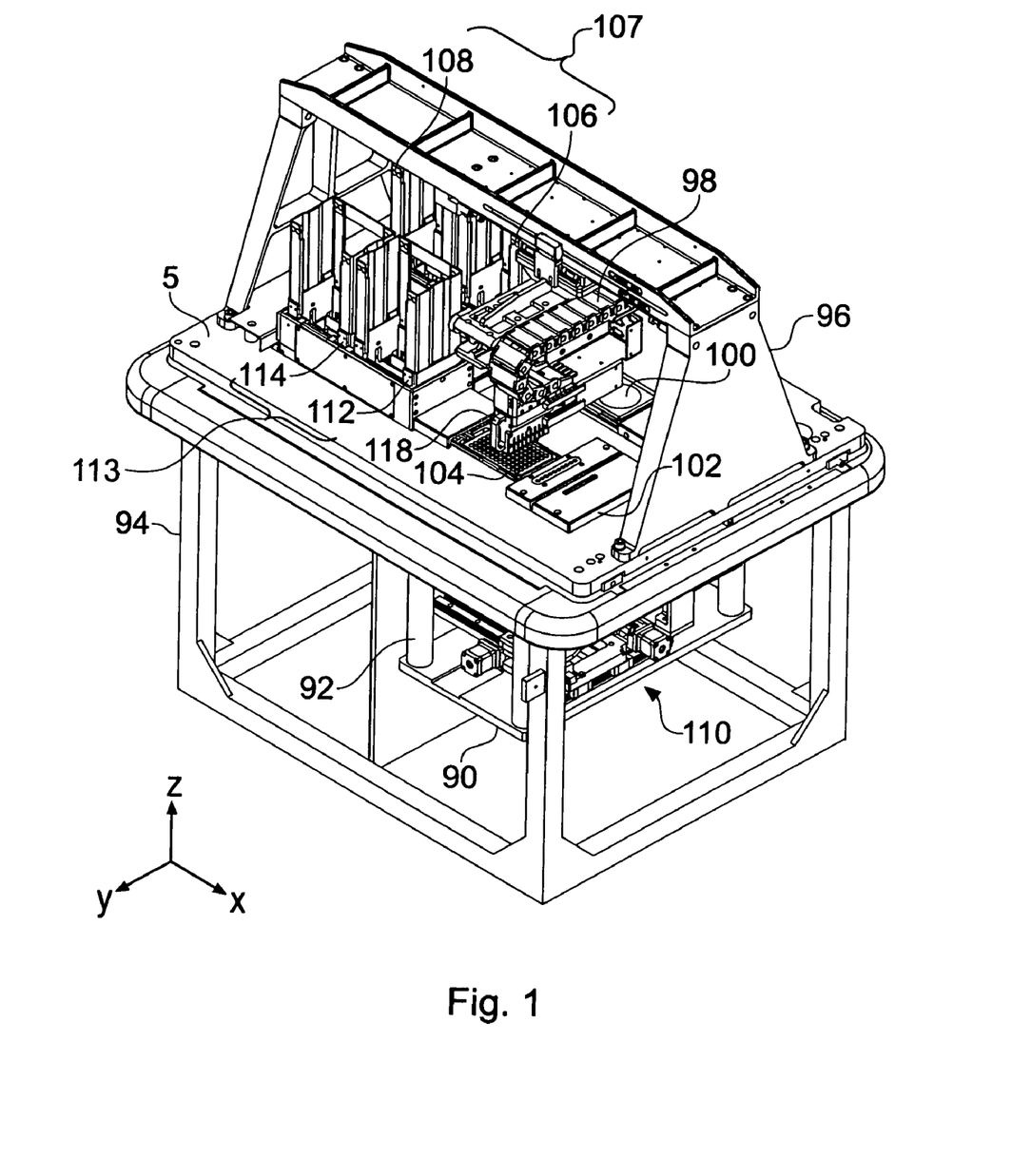
FIG. 1 is a perspective view of an apparatus embodying the invention.

FIG. 1 is a perspective view of an apparatus embodying the invention. The apparatus may be considered to be a robot for picking, gel coring or other biological manipulation task with integrated fluorescence excitation and collection (i.e. detection) optics. The apparatus can be subdivided notionally into two half spaces existing above and below a main bed 5 which is supported by a frame 94.

Above the main bed 5, the apparatus appears as similar to a conventional picking robot. A cell picking head 118 is provided that comprises a plurality of hollow pins for aspirating animal cells. The cell picking head 118 is movable over the main bed 5 by a head position system made up of x- y- and z-linear positioners 98 connected in series and suspended from a gantry 96. A wash/dry station 102 is also provided on the main bed 5 for cleansing the pins. The whole upper half space of the apparatus will typically be enclosed in a housing (not shown) including a hinged door extending over one side and part of the top of the apparatus.

Below the main bed 5, an optics sub-assembly 110 is provided to accommodate fluorescence excitation and detection optics system which is mounted on a tray 90 suspended from the main bed 5 by pillars 92. The under-slung optics system is arranged to view well plates placed on the imaging station 100.

The main bed 5 is provided with two main working stations, namely an imaging station 100 and a replating station 104, each of which is positioned at the end of a respective well plate feed lane. Each well plate feed lane has a well plate feeder/stacker. The well plate feeder/stacker 107 for the imaging station 100 has a well plate feed storage cassette 106 and well plate (re-)stack storage cassette 108. A stack of well plates are held in the feed storage cassette 106, fed in turn down the lane via a delidder (not shown) to the imaging station 100, returned back along the lane, relidded and passed into the rear storage cassette 108. A similar well plate feeder/stacker 113 is used for the other lane to supply well plates from the storage cassette 112 to the replating station 104 and back along the lane to the (re-)stack storage cassette 114.

The well plate feeder/stacker mechanisms including delidding are described fully in EP-A-1 293 783 [2], the contents of which are incorporated herein by reference.

The cell picking head 118 can thus be moved from the imaging station to the replating station to allow replating of animal cells from a target well plate to a destination well plate. In the illustrated embodiment, there is only one destination lane. However, it may be desirable in some cases to have 2, 3 or 4 destination lanes. This may be useful when it is desired to split the animal cells from a given target well into multiple destination wells. The feeder/stacker mechanism is fully modular, so the number of well plate feed lanes can be increased without difficulty.

Figure 2:
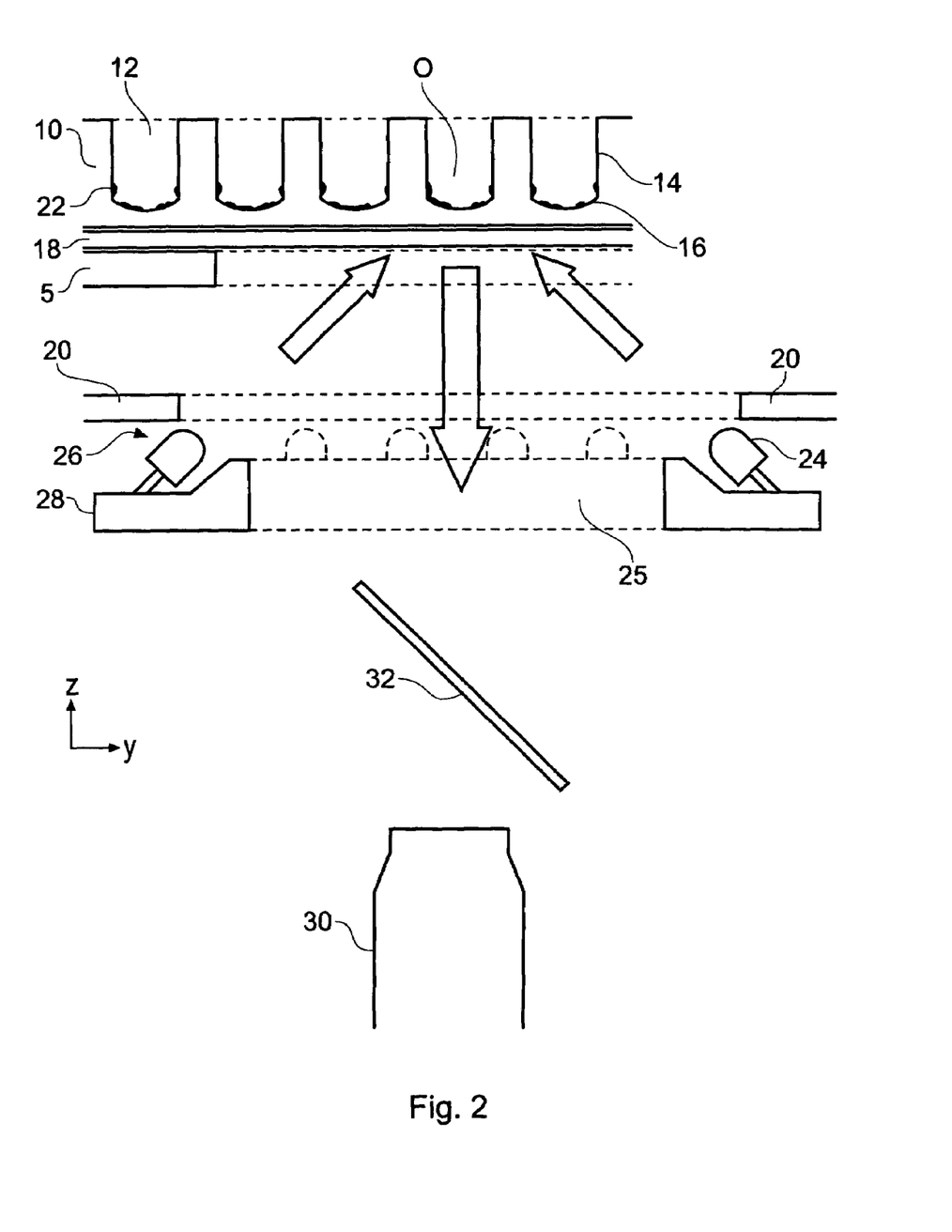
FIG. 2 is a schematic sectional side view showing the sample excitation and collection paths in the vicinity of the sample using a well plate as an example sample container.

FIG. 2 is a schematic sectional side view showing principles of the design of the optical sub-assembly 110. Part of a well plate 10 showing 5 wells is also shown. It will be appreciated that samples in other containers may also be studied. Adherent colonies 22 have been cultured in the wells also as shown, the colonies forming around the base 16 and lower sidewalls 14 of the wells 12. The imaging station is formed in an aperture in the main bed 5 covered by a sheet of optically transparent material, typically glass, that forms a light table 18. For optical analysis, a well plate 10 is arranged on the light table 18 as shown, having been deposited there by the well plate feeder/stacker. The apparatus is designed to image one well at a time. To image a specific well 12 of a well plate, the optical sub-assembly 110 is aligned relative to the well 12.

The optical sub-assembly 110 comprises two illumination sources and a collection part.

The first illumination source is formed of a plurality of white light emitting diodes (LEDs) 24 arranged to form an LED ring 26 located in a collar 28 with a central aperture 25 with the optical axes of the LEDs lying on the surface of a common cone, the point of which is coincident and labeled as the object position O in the figure. This white light source is provided principally to collect conventional images of the sample, for example as are used for performing cell confluence detection by image processing techniques. An apertured top plate 20 lying above the LED ring 26 is also illustrated. This is a structural component and has no significance for the optical design.

This second illumination source (not shown in this figure) is arranged to illuminate from the side, as shown by the sideways arrow, onto a semi-silvered mirror 32 which deflects the excitation light vertically onto the sample, as shown by the upwardly pointing arrow, in order to perform fluorescence measurements.

The collection part of the optical sub-assembly is made up of a zoom lens 30 with autofocus and is used to collect light when either (or both) of the illumination sources is used. The optical axis is vertical and coincident with the object position O.

The well to be imaged is thus aligned laterally with the optical axis of the collection optics and the fluorescence excitation optics and laterally and vertically with the center point of the white light lateral illumination, whereby the center point of the lateral illumination is around the base of the well or slightly higher as illustrated. The LEDs 24 thus illuminate a well 12 arranged in the object position O at an oblique angle from below so that an image of the well 12 is taken in a dark field configuration where light from the LEDs, if not scattered, does not contribute to the well image gathered by the collection lens 30.

Figure 3:
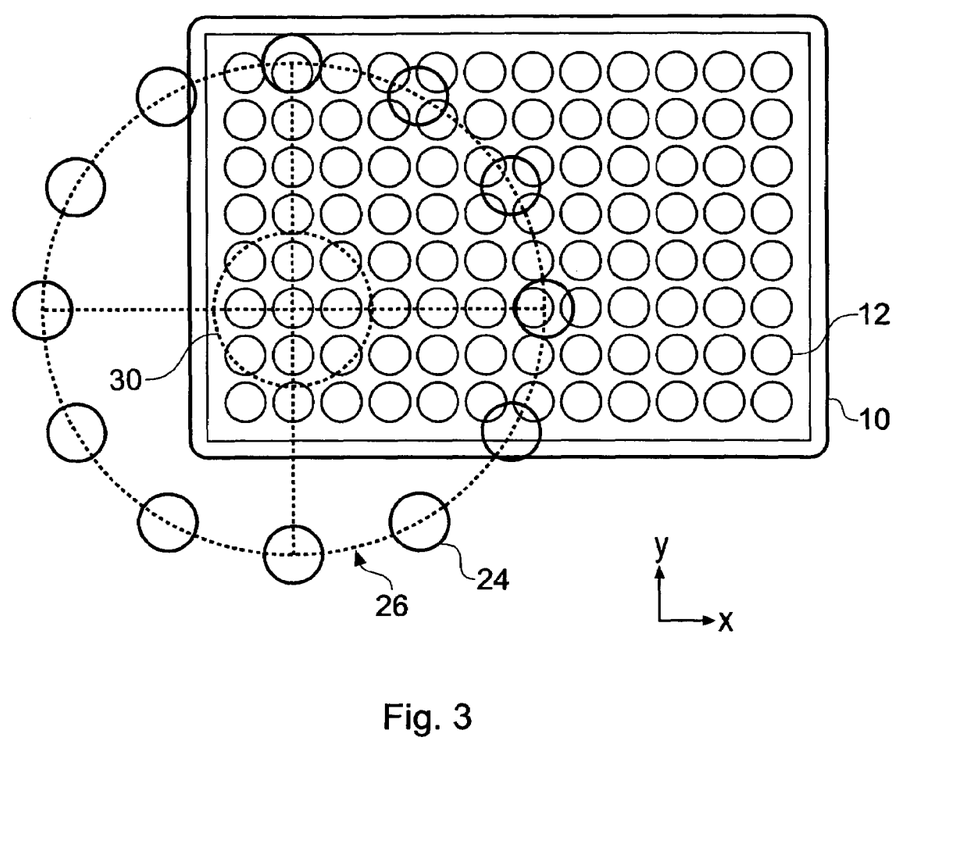
FIG. 3 is a schematic plan view of the sample vicinity with a well plate as the sample container.

FIG. 3 is a schematic plan view of selected parts of the optical system shown in FIG. 2. The well plate 10 is a 96 well version and is shown aligned with the optical sub-assembly 110 so that a well 12 three rows up (row m=3) and two columns along (column n=2) is targeted, as illustrated by the objective lens 30 and LED ring 26 of LEDs 24. The optical sub-assembly is arranged on x- and y-positioners so that the collection lens 30 and illumination ring 26 can be moved together to image any one of the wells 12. Typically, the wells will be imaged in sequence row-wise and column-wise with a rastering process. This is achieved by moving the optical sub-assembly while the well plate remains static which is preferable so that liquid in the wells is not shaken by moving the well plate between imaging each well which might have an adverse influence on the imaging.

Figure 4A:
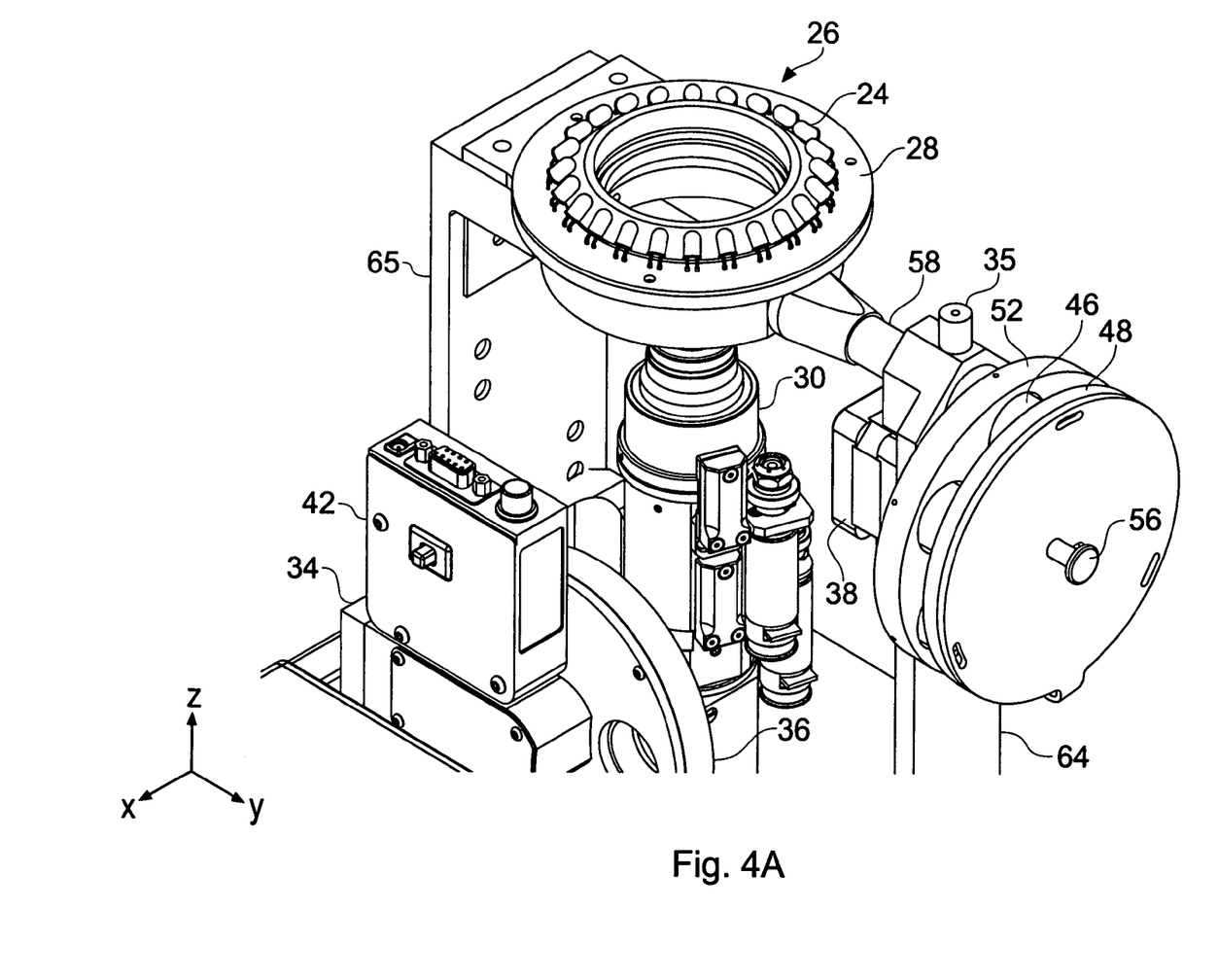
FIGS. 4A, 4B and 4C are perspective and orthogonal side views of the optics sub-assembly arranged below the main bed of the apparatus of FIG. 1.
Figure 4B:
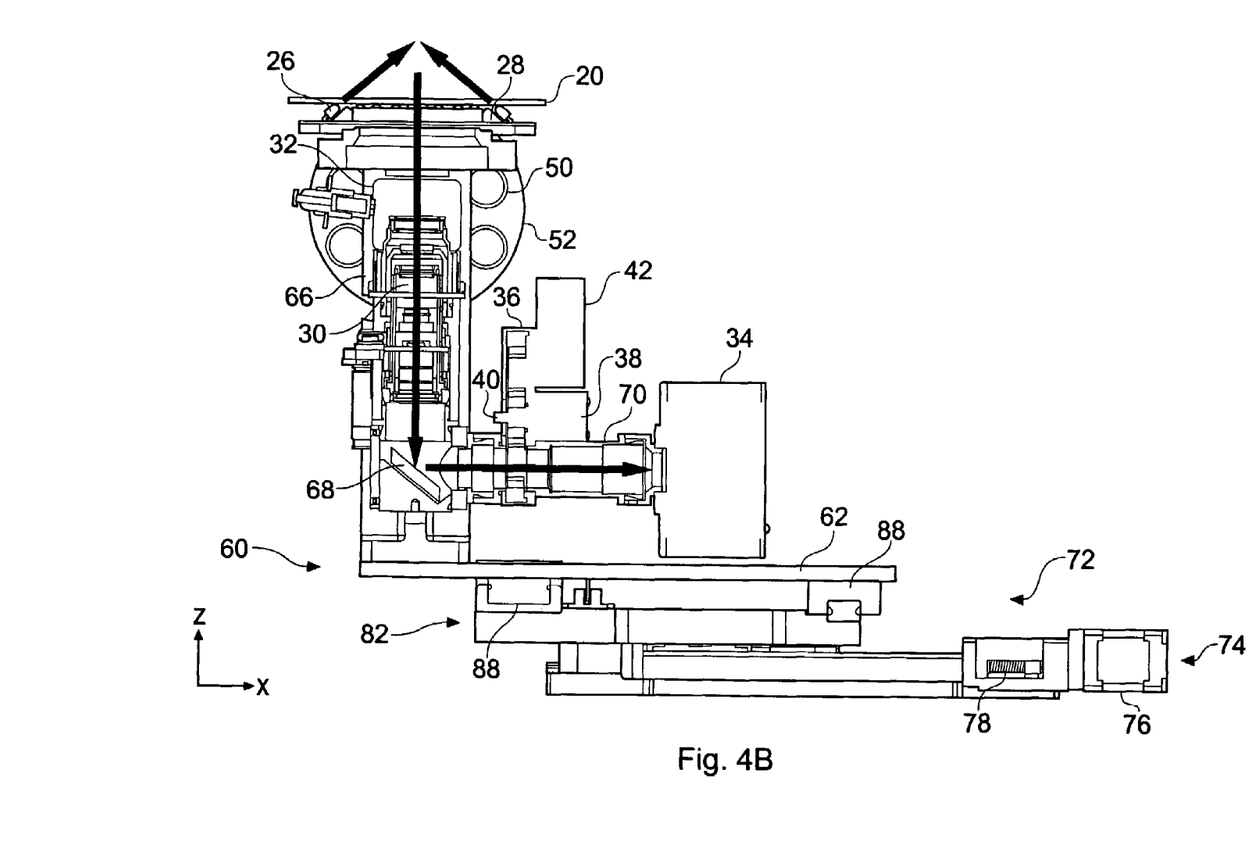
Figure 4C:
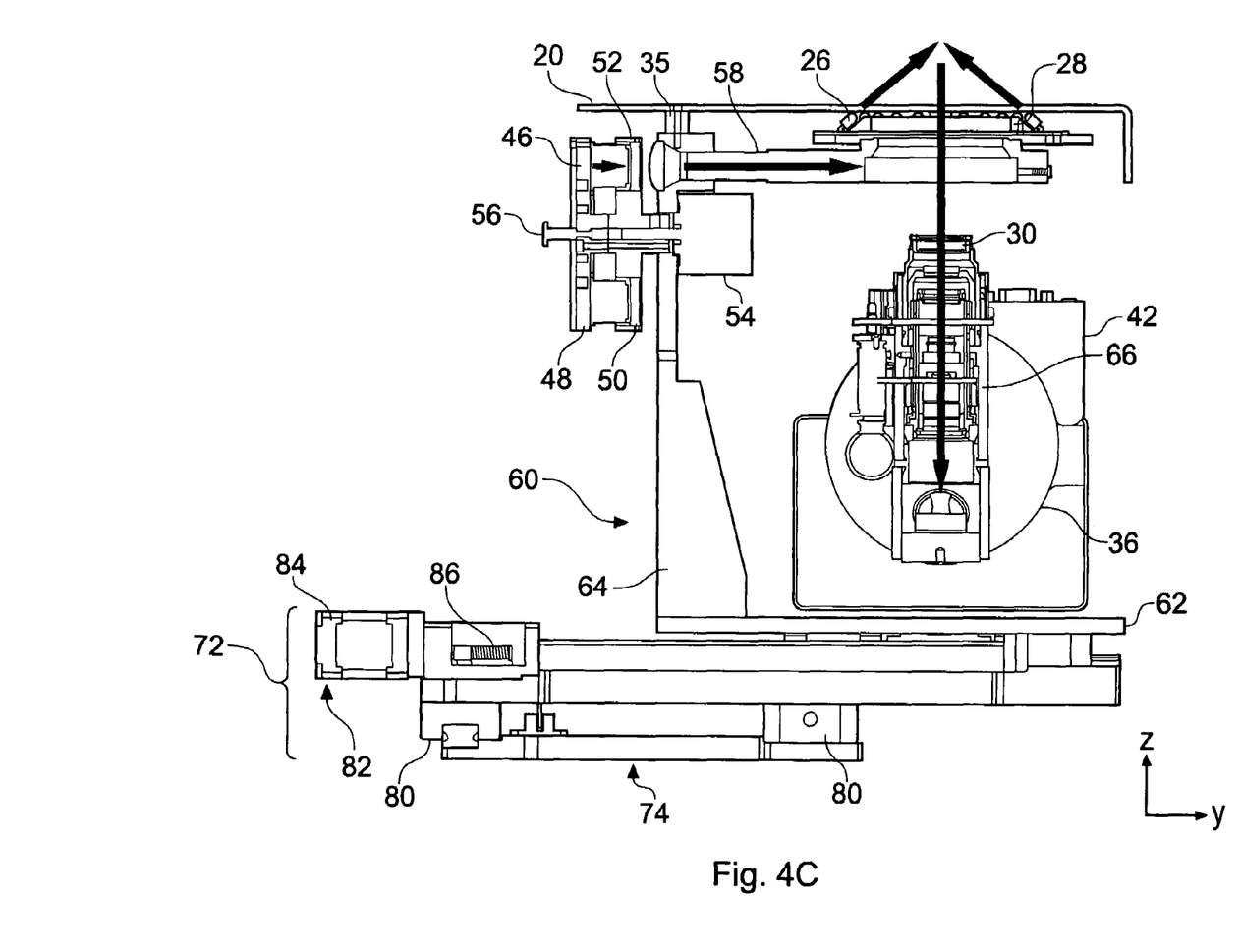

FIGS. 4A, 4B and 4C are perspective and orthogonal side views of the optics sub-assembly arranged below the main bed of the apparatus of FIG. 1. These three figures are described together, rather than in turn, since they are different views of the same equipment, noting that not all features are visible or marked with reference numerals in each figure.

The previously described collar-mounted LED ring 24, 26, 28 is evident in all three figures. The LED collar 28 is cantilevered out on a side bracket from a vertical mounting plate 65 (FIG. 4A) which is part of a frame 60. The vertical mounting plate 65 is upstanding from a base plate 62.

The fluorescence excitation optics is mounted on the base plate 62 via a further vertical mounting plate 64. The excitation source is colored LEDs 44 (not shown) that are arranged in groups of different colors 46 on a wheel 48 which is a converted filter wheel with LED groups 46 arranged at each filter position. In front of each LED group 46 there is a bandpass or other suitable narrowband filter 50 (see FIGS. 4B & 4C) each arranged in the filter position of a further filter wheel 52 arranged coaxially and on the same motor spindle 56 as the filter wheel 48, the two wheels being driven in unison by a motor 54. Each bandpass filter 50 is selected to transmit a range of wavelengths matched to the emission wavelength band of the LED group 46 with which it is paired. Light from the uppermost LED group 46 is directed horizontally through a light pipe 58, which is not a waveguide, merely a shroud for preventing light spillage, onto the semi-silvered mirror 32 (see FIG. 4B and also FIG. 2) which serves as a beam splitter for directing a portion of the colored LED light through the LED collar's aperture 25 to the object position. Other forms of beam splitter could also be used, for example a cubic beam splitter. The beam-splitter is preferably removable, or movable away from the aperture 25 so that when lateral illumination from the colored LED groups is not needed, it can be taken out of the collection path so that it does not result in loss of collected signal. A mounting stub 35 is also evident in FIGS. 4A and 4C. This mounting stub 35 is for connecting the colored LED group features to the top plate 20 (removed in FIG. 4A, but shown in FIGS. 4B and 4C and also FIG. 2).

The collection lens 30 is held vertically in a mounting tube 66 (see FIGS. 4B & 4C) at the base of which is arranged a plane deflecting mirror 68 which redirects the collected light horizontally and supplies it along a light pipe 70 to a CCD camera 34. Part way along the light pipe 70 there is arranged a filter wheel 36 mounted on a spindle 40 and driven by a motor 38. Drive electronics for the filter wheel 36 are housed in a unit 42. Typically filters will be used in the collection optics to filter out excitation light from the colored LED groups 46 when spectroscopic measurements are being performed. Collection side filters 45 may also be useful for filtering out fluorescence, e.g. to stop fluorescence from swamping out contrast of the cell periphery. This might be auto-fluorescence or fluorescence from a tag. For straight-forward confluence detection using the white LEDs 24, no filter may be needed on the collection side.

The optical components are thus all mounted directly or indirectly on the base plate 62. The base plate 62 is carried by a linear positioner 82 which is in turn carried by a linear positioner 74 to provide xy-motion for the whole optical set-up. In the illustration, the x-positioner 74 is at the bottom with the y-positioner mounted on top of it. However, it will be appreciated this choice is arbitrary. It will also be appreciated that a parallel mechanism xy-positioner could be provided instead of two piggy-backed linear positioners. The x-positioner 74 comprises a motor 76, lead screw 78 and a pair of sets of guide bearings 80. The y-positioner 82 is the same, comprising a motor 84, lead screw 86 and a pair of sets of guide bearings 88.

As an alternative to having colored LED of different colors arranged in filter positions on a filter wheel as described above, it is possible to have concentric rings of different colors of LED in a single mounting. For example, the white light LED ring could be exchanged or supplemented with a number of LED rings of different colors. In principle an arbitrary arrangement of LEDs of different colors would provide the same functionality so long as LEDs of different colors could be driven independently, but would be a less elegant design. It would also be possible to use a single group of broadband LEDs in combination with filtering. However, this approach would tend to provide less illumination power than using different colors of LED. It will also be appreciated that other optical sources could be used including superfluorescent LEDs or diode lasers. Fixed wavelength or tunable diode lasers may be used.

By way of example, the table below gives, for a number of useful dyes, suitable LED types for the excitation LED groups 46 together with suitable pairs of excitation side filters 50 and collection-side (i.e. emission) filters 45. The peak excitation and emission wavelengths λ of the example dyes are also stated.

| Dye | Peak Excitation λ (nm) | Peak Emission λ (nm) | LED Type | Excitation Filter | Emission Filter (Chroma Co.) |
|---|---|---|---|---|---|
| BFP | 381 | 445 | UV | none | D460/50 m |
| CFP | 434 | 477 | Royal Blue | D(HQ)450/50x | D505/40 m |
| EGFP | 488 | 507 | Blue | D(HQ)470/40x | HQ535/50 m |
| FITC | 490 | 525 | Blue | D(HQ)470/40x | HQ535/50 m |
| YFP | 513 | 527 | Cyan | D(HQ)500/30x | D550/40 m |
| Rhodamine | 550 | 573 | Green | D(HQ)530/30x | HQ590/50 m |
| DSRed | 565 | 582 | Green | D(HQ)530/30x | HQ590/50 m |
| Cy5 | 649 | 670 | Red | D(HQ)623/36x | HQ700/75 m |

Figure 5:
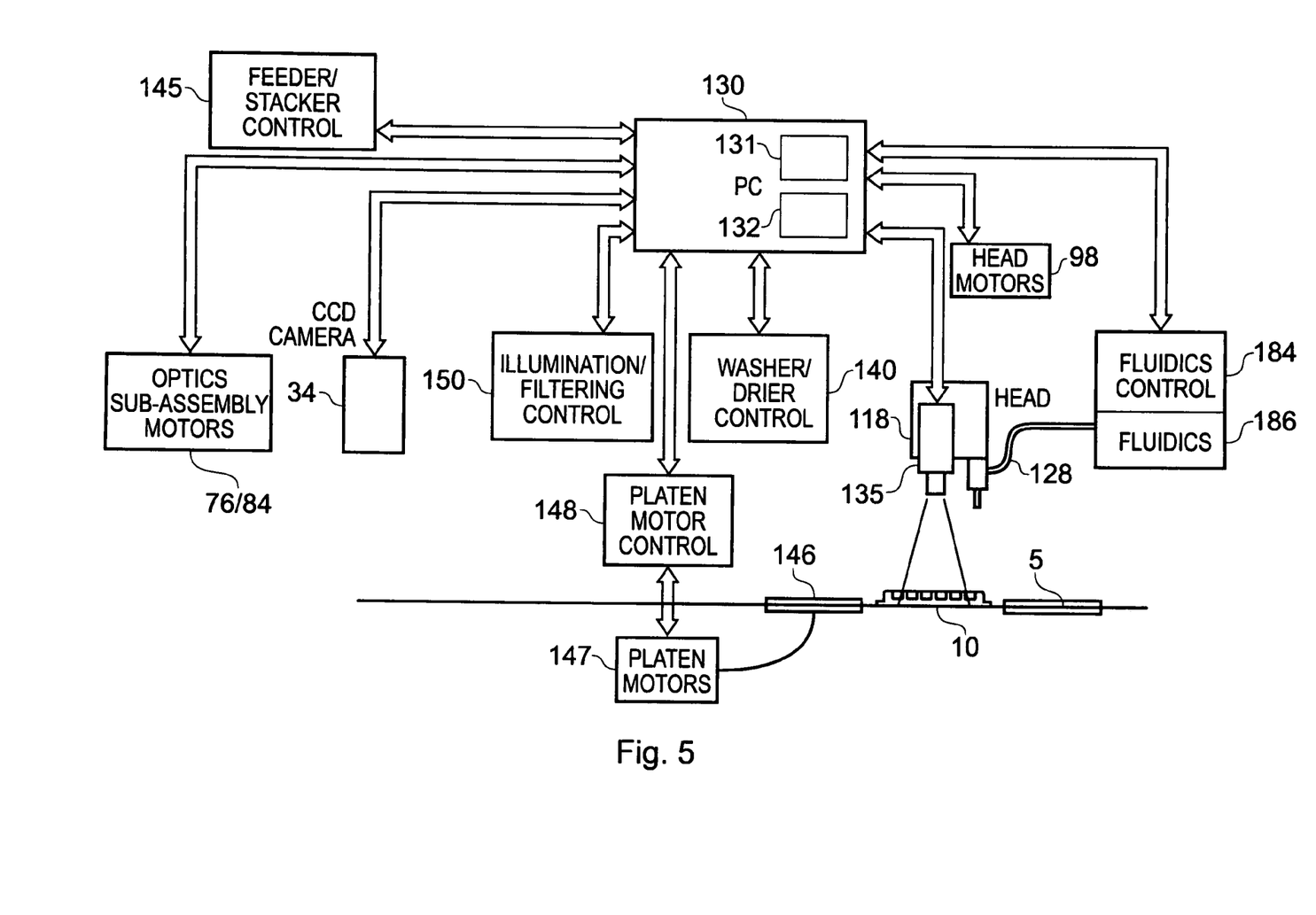
FIG. 5 is a block schematic diagram showing the control system of the apparatus.

FIG. 5 is a block schematic diagram showing the control system of the apparatus for coordinating the various components to perform the processes described above. A computer (PC 130) is used as the principal control component and is connected by electronic links using standard interfacing protocols to the various components that are part of the automated control system. The control is effected by control software 131 resident in the PC 130. Image processing and spectroscopic analysis software 132 is also resident in the PC 130 and linked to the control software 131. The image processing and spectroscopic analysis may also be carried out in hardware or firmware if desired. The CCD camera 34 is connected to the PC 130 for receiving digital images captured by the camera 34. An illumination and filter controller 150 is connected to the PC 130 for controlling the various under-bed optical sources and filter wheels of the optical sub-assembly 110. A washer/drier controller 140 is connected to the PC 130 and used to control the blower and the halogen lamps of the wash/dry station 102. The positioners 98 for moving the head 118 are connected to the PC 130. The PC 130 is also connected to the motors 76 and 84 of the x- and y-positioners of the under-bed optics sub-assembly 110. A head-mounted camera 135 is also provided for machine vision, such as bar-code detection on well plates, and is connected to the PC 130 for receiving digital images captured by the head-mounted camera 135. These are used for aligning the pins of the head with the various locations of interest such as the wash/dry station 102, well plates etc. The fluid lines 128 are connected to the fluidics unit 186 which is controlled by the fluidics control unit 184 connected to the PC 130. The fluidics control unit 184 is used to control the pressure in the fluid lines to allow aspiration, retention and expulsion of liquid from the sample. The fluidics control unit 184 also controls the wash cycle of the pins and fluid lines, whereby cleaning fluid from the baths is aspirated and expelled from the ends of the pins during the cleaning cycle. A feeder/stacker control unit 145 is also provided for the feeder/stacker units, including the well plate supply lanes, and is connected to the PC 130. Separate units 145 may be provided for each lane in view of the modular nature of the feeder/stacker assemblies. The figure also illustrates schematically an optional feature whereby a carrier in the form of a platen 146 is provided to carry one or more well plates 10 or other biological sample containers. The platen 146 is movable in the x- and y-directions by associated motors 147 and motor controller unit 148 which is connected to the PC 130, these elements collectively forming a positioning system for well plates or other containers arranged on the apparatus. The platen can then be moved in a controlled fashion to allow well-by-well iterative scanning by the optical system across all wells of a well plate. The platen may be provided with an integral heating element, so that well plates or other biological sample containers carried by the platen can be maintained at elevated temperatures, for example to promote enzymatic activity in the samples.

It will thus be appreciated that lateral positioning can be achieved in a variety of ways either by moving the optical source and detector on a common platform under the bed of the apparatus, moving the sample with its own xy-positioning system on the sample carrier, or by moving the head. In any given apparatus or process, various combinations of these motion systems may be used.

It will be understood that although the control system described above is specific to a robot for gel coring, the invention is applicable to any robot of the arraying type, such as used for colony picking, liquid handling etc., in that the under-bed mounted combined excitation and collection optics can be provided for any robotic head arrangements for micro-arraying or related applications for automated manipulation of well plates and other types of biological sample container.

It will be appreciated that although particular embodiments of the invention have been described, many modifications/additions and/or substitutions may be made within the spirit and scope of the present invention.

REFERENCES

1. EP-A-1 391 719 (Genetix Limited)
2. EP-A-1 293 783 (Genetix Limited)

What is claimed is:

1. A robotic apparatus comprising:
   a main bed fitted with an imaging station where a sample container containing a plurality of cells or cell colonies can be placed in an object position;
   a cell picking head comprising a plurality of pins for performing cell picking, the cell picking head having an associated positioning system mounted above the main bed of the apparatus; and
   excitation and collection optical sub-systems mounted under the main bed of the apparatus and arranged to excite, and collect light from, the object position from below.

2. The apparatus of claim 1, wherein the excitation optical sub-system is controllable to provide excitation at any one of a plurality of different wavelengths for selectively exciting a plurality of different dyes of interest.

3. The apparatus of claim 1, wherein the excitation optical sub-system comprises a plurality of different bandpass filters for selecting light at different wavelengths for selectively exciting a plurality of different dyes of interest.

4. The apparatus of claim 1, wherein the excitation optical sub-system comprises a white light source.

5. The apparatus of claim 1, wherein the collection optical sub-system comprises a plurality of different filters for assisting collection of light at different emission wavelengths associated with fluorescence from a plurality of different dyes of interest.

6. The apparatus of claim 1, an optics positioning system for aligning the excitation and collection optical sub-systems relative to the object position so that any one of a plurality of desired locations of the sample container can be moved into the object position.

7. The apparatus of claim 1, comprising a sample container feeder/stacker operable to supply each of a plurality of sample containers from a feed and return them to a stack.

8. The apparatus of claim 6, wherein the sample container is a well plate, and the desired locations are locations of wells in the well plate.

9. The apparatus of claim 6, wherein the desired locations are locations of cells or cell colonies in the sample container.

10. The apparatus of claim 1, wherein the pins are hollow pins for aspirating the cells or cell colonies.

11. The apparatus of claim 1, wherein the pins are solid or split pins for picking cells or cell colonies.

12. A robotic apparatus comprising:
    a main bed fitted with an imaging station where a sample container containing a sample can be placed in an object position;
    a head with associated positioning system mounted above the main bed of the apparatus; and
    excitation and collection optical sub-systems mounted under the main bed of the apparatus and arranged to excite, and collect light from, the object position from below, wherein the excitation optical sub-system comprises a plurality of different types of optical source of different emission wavelengths for selectively exciting a plurality of different dyes of interest.

13. The apparatus of claim 12, wherein the sample is a plurality of cells or cell colonies.

14. The apparatus of claim 12, wherein the head is a cell picking head comprising a plurality of pins for performing cell picking.

15. The apparatus of claim 14, wherein the pins are hollow pins for aspirating the cells or cell colonies.

16. The apparatus of claim 14, wherein the pins are solid or split pins for picking cells or cell colonies.

17. The apparatus of claim 12, wherein the excitation optical sub-system is controllable to provide excitation at any one of a plurality of different wavelengths for selectively exciting a plurality of different dyes of interest.

18. The apparatus of claim 12, wherein the excitation optical sub-system comprises a plurality of different bandpass filters for selecting light at different wavelengths for selectively exciting a plurality of different dyes of interest.

19. The apparatus of claim 12, wherein the excitation optical sub-system comprises a white light source.

20. The apparatus of claim 12, wherein the collection optical sub-system comprises a plurality of different filters for assisting collection of light at different emission wavelengths associated with fluorescence from a plurality of different dyes of interest.

21. The apparatus of claim 12, an optics positioning system for aligning the excitation and collection optical sub-systems relative to the object position so that any one of a plurality of desired locations of the sample container can be moved into the object position.

22. The apparatus of claim 21, wherein the sample container is a well plate, and the desired locations are locations of wells in the well plate.

23. The apparatus of claim 21, wherein the desired locations are locations of cells or cell colonies in the sample container.

24. A robotic apparatus comprising:
    a main bed fitted with an imaging station where a sample container containing a sample can be placed in an object position;
    a head with associated positioning system mounted above the main bed of the apparatus; and excitation and collection optical sub-systems mounted under the main bed of the apparatus and arranged to excite, and collect light from, the object position from below, wherein the excitation optical sub-system comprises at least one optical source arranged to illuminate the object position at an oblique angle.

25. The apparatus of claim 24, wherein the collection optical sub-system is arranged to collect light from the object position such that the light is collected in a dark field configuration where light from the at least one optical source, if not scattered, does not contribute to the collected signal.

26. The apparatus of claim 24, wherein the sample is a plurality of cells or cell colonies.

27. The apparatus of claim 24, wherein the head is a cell picking head comprising a plurality of pins for performing cell picking.

28. The apparatus of claim 27, wherein the pins are hollow pins for aspirating the cells or cell colonies.

29. The apparatus of claim 27, wherein the pins are solid or split pins for picking cells or cell colonies.

30. The apparatus of claim 24, wherein the excitation optical sub-system is controllable to provide excitation at any one of a plurality of different wavelengths for selectively exciting a plurality of different dyes of interest.

31. The apparatus of claim 24, wherein the excitation optical sub-system comprises a plurality of different bandpass filters for selecting light at different wavelengths for selectively exciting a plurality of different dyes of interest.

32. The apparatus of claim 24, wherein the excitation optical sub-system comprises a white light source.

33. The apparatus of claim 24, wherein the collection optical sub-system comprises a plurality of different filters for assisting collection of light at different emission wavelengths associated with fluorescence from a plurality of different dyes of interest.

34. The apparatus of claim 24, an optics positioning system for aligning the excitation and collection optical sub-systems relative to the object position so that any one of a plurality of desired locations of the sample container can be moved into the object position.

35. The apparatus of claim 34, wherein the sample container is a well plate, and the desired locations are locations of wells in the well plate.

36. The apparatus of claim 34, wherein the desired locations are locations of cells or cell colonies in the sample container.

37. A robotic apparatus comprising:
a main bed fitted with an imaging station where a sample container containing a sample can be placed in an object position;
a head with associated positioning system mounted above the main bed of the apparatus; and
excitation and collection optical sub-systems mounted under the main bed of the apparatus and arranged to excite, and collect light from, the object position from below, wherein the excitation optical sub-system comprises a plurality of directional light emitting units arranged to emit beams having optical axes lying on the surface of a common cone, the point of which is coincident with the object position.

38. The apparatus of claim 37, wherein the sample is a plurality of cells or cell colonies.

39. The apparatus of claim 37, wherein the head is a cell picking head comprising a plurality of pins for performing cell picking.

40. The apparatus of 39, wherein the pins are hollow pins for aspirating the cells or cell colonies.

41. The apparatus of 39, wherein the pins are solid or split pins for picking cells or cell colonies.

42. The apparatus of claim 37, wherein the excitation optical sub-system is controllable to provide excitation at any one of a plurality of different wavelengths for selectively exciting a plurality of different dyes of interest.

43. The apparatus of claim 37, wherein the excitation optical sub-system comprises a plurality of different bandpass filters for selecting light at different wavelengths for selectively exciting a plurality of different dyes of interest.

44. The apparatus of claim 37, wherein the excitation optical sub-system comprises a white light source.

45. The apparatus of claim 37, wherein the collection optical sub-system comprises a plurality of different filters for assisting collection of light at different emission wavelengths associated with fluorescence from a plurality of different dyes of interest.

46. The apparatus of claim 37, an optics positioning system for aligning the excitation and collection optical sub-systems relative to the object position so that any one of a plurality of desired locations of the sample container can be moved into the object position.

47. The apparatus of claim 46, wherein the sample container is a well plate, and the desired locations are locations of wells in the well plate.

48. The apparatus of claim 46, wherein the desired locations are locations of cells or cell colonies in the sample container.

49. A robotic apparatus comprising:
a main bed fitted with an imaging station where a sample container containing a sample can be placed in an object position;
a head with associated positioning system mounted above the main bed of the apparatus; and
excitation and collection optical sub-systems mounted under the main bed of the apparatus and arranged to excite, and collect light from, the object position from below, wherein the optical source comprises a plurality of directional light emitting units arranged to emit beams having optical axes lying on the surface of at least two cones whose points are coincident with each other and the object position.

50. Use of a robot equipped with a head for manipulating biological samples, the use comprising:
providing a sample container containing at least one cell;
arranging the sample container at an imaging station;
making a spectroscopic measurement by illuminating the at least one cell from below and collecting light from the at least one cell also from below; and
manipulating the at least one cell with the head based on the spectroscopic measurement.

51. The use of claim 50, wherein the spectroscopic measurement is based on a fluorescent agent.

52. The use of claim 51, wherein the fluorescent agent is a dye.

53. The use of claim 52, wherein the dye is contained in the at least one cell.

54. The use of claim 52, wherein the at least one cell is contained in a medium which is marked with the dye whose optical activity is modified by secretion from the at least one cell.

55. The use of claim 54, wherein the secretion is a protein, nucleic acid, lipid, sugar, metabolite or drug.

56. The use of claim 54, wherein the spectroscopic measurement detects fluorescence, white light, infra-red, by Raman spectroscopy, or auto-fluorescence.

57. The use of claim 51, wherein the fluorescent agent is an inherent part of the cell.

58. The use of claim 50, wherein the at least one cell is an animal cell.

59. The use of claim 58, wherein the at least one animal cell express a biological molecule of interest.

60. The use of claim 59, wherein the biological molecule of interest is selected from the group consisting of: a peptide, a polypeptide, a nucleic acid, a lipid, a metabolyte, a glycosylated or unglycosylated protein, and a biopharmaceutical protein.

61. The use of claim 51, wherein the fluorescent agent is selected from the group consisting of: a protein, a nucleic acid, a lipid, a sugar, a metabolite, and a drug.

62. The use of claim 51, wherein the fluorescent agent is detected by white light or infra-red.

63. The use of claim 50, wherein the spectroscopic measurement is based on a Raman agent.

64. The use of claim 51 wherein the at least one cell is a protein, nucleic acid, lipid, sugar or metabolite.

65. The use of claim 51, wherein the at least one cell secretes an agent which is detected by white light, infra-red, or Raman spectroscopy.

66. The use of claim 51, wherein the at least one cell secretes an agent which is detected by addition to the at least one cell of a compound that is detected by autofluorescence.

67. The use of claim 51, wherein the at least one cell contains an agent detected by addition to the at least one cell of a compound that is detected by fluorescence, white light, infra-red, Raman spectroscopy, or autofluorescence.

68. The use of claim 51, wherein the at least one cell secretes an agent detected by addition to the at least one cell of a compound that is detected by fluorescence, white light, infra-red, Raman spectroscopy, or autofluorescence.

69. The use of claim 51, wherein the at least one cell has a membrane which contains an agent which is detected by addition to the at least one cell of a compound that is detected by fluorescence, white light, infra-red, Raman spectroscopy, or autofluorescence.

* * * * *